(12) United States Patent
Edic et al.

(10) Patent No.: US 9,949,650 B2
(45) Date of Patent: *Apr. 24, 2018

(54) FRACTIONAL FLOW RESERVE ESTIMATION

(71) Applicants: General Electric Company, Schenectady, NY (US); University of Michigan, Ann Arbor, MI (US)

(72) Inventors: Peter Michael Edic, Albany, NY (US); Robert Franklin Senzig, Germantown, WI (US); Kai Erik Thomenius, Clifton Park, NY (US); Steven James Gray, Elm Grove, WI (US); David Allen Langan, Clifton Park, NY (US); Prem Venugopal, Niskayuna, NY (US); Jeffrey Brian Fowlkes, Ann Arbor, MI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 530 days.

This patent is subject to a terminal disclaimer.

(21) Appl. No.: 13/842,104

(22) Filed: May 6, 2013

(65) Prior Publication Data

US 2014/0005535 A1    Jan. 2, 2014

Related U.S. Application Data

(63) Continuation of application No. 13/408,886, filed on Feb. 29, 2012.

(51) Int. Cl.
*A61B 5/00* (2006.01)
*A61B 5/026* (2006.01)
(Continued)

(52) U.S. Cl.
CPC .......... *A61B 5/026* (2013.01); *A61B 5/02007* (2013.01); *A61B 6/504* (2013.01);
(Continued)

(58) Field of Classification Search
CPC ..... A61B 5/02007; A61B 5/026; A61B 6/032; A61B 6/4078; A61B 6/4085;
(Continued)

(56) References Cited

U.S. PATENT DOCUMENTS

| 5,647,360 A | 7/1997 | Bani-Hashemi et al. |
| 6,236,878 B1 | 5/2001 | Taylor et al. |

(Continued)

OTHER PUBLICATIONS

JT Wong et al. "Determination of fractional flow reserve (FFR) based on scaling laws: a simulation study." Phys. Med. Biol. 53 (2008) 3995-4011.*

(Continued)

*Primary Examiner* — Amanda Lauritzen Moher
(74) *Attorney, Agent, or Firm* — Pabitra K. Chakrabarti

(57) ABSTRACT

Approaches for assessing hemodynamic characteristics for an organ of interest are related. In one implementation, a fluid dynamics model may be provided with data derived from an anatomic imaging modality and blood flow information derived by ultrasound to derive the desired hemodynamic characteristics. In one such implementation, a fractional flow reserve is estimated.

23 Claims, 5 Drawing Sheets

(51) Int. Cl.
*A61B 8/06* (2006.01)
*A61B 5/02* (2006.01)
*A61B 6/03* (2006.01)
*A61B 6/00* (2006.01)
*A61B 8/08* (2006.01)
*G06F 19/00* (2018.01)
*G06F 17/50* (2006.01)

(52) U.S. Cl.
CPC ............ *A61B 6/507* (2013.01); *A61B 6/5217* (2013.01); *A61B 8/06* (2013.01); *A61B 8/5223* (2013.01); *A61B 6/032* (2013.01); *A61B 6/4078* (2013.01); *A61B 6/4085* (2013.01); *A61B 6/4441* (2013.01); *A61B 6/481* (2013.01); *A61B 6/503* (2013.01); *A61B 6/5247* (2013.01); *A61B 6/5288* (2013.01); *A61B 8/0883* (2013.01); *A61B 8/0891* (2013.01); *A61B 8/488* (2013.01); *A61B 8/5261* (2013.01); *A61B 8/5284* (2013.01); *G06F 17/5009* (2013.01); *G06F 19/3437* (2013.01); *G06F 2217/16* (2013.01)

(58) Field of Classification Search
CPC ....... A61B 6/4441; A61B 6/481; A61B 6/503; A61B 6/504; A61B 6/507; A61B 6/5217; A61B 6/5247; A61B 6/5288; A61B 8/06; A61B 8/0883; A61B 8/0891; A61B 8/488; A61B 8/5223; A61B 8/5261; A61B 8/5284; G06F 17/5009; G06F 19/3437; G06F 2217/16
See application file for complete search history.

(56) References Cited

U.S. PATENT DOCUMENTS

| | | | |
|---|---|---|---|
| 7,138,104 B2 | 11/2006 | Carpenter, Jr. | |
| 7,481,789 B2* | 1/2009 | Assmann | G06T 7/11 |
| | | | 382/128 |
| 7,744,537 B2 | 6/2010 | Kanai et al. | |
| 7,828,735 B2 | 11/2010 | Holmes et al. | |
| 7,963,925 B1 | 6/2011 | Schecter | |
| 8,315,812 B2* | 11/2012 | Taylor | 702/19 |
| 8,915,860 B2 | 12/2014 | Blankfield | |
| 9,538,925 B2* | 1/2017 | Sharma | A61B 5/0261 |
| 2003/0083582 A1 | 5/2003 | Hirsh | |
| 2003/0191392 A1* | 10/2003 | Haldeman | 600/467 |
| 2006/0020200 A1 | 1/2006 | Medow et al. | |
| 2006/0034508 A1 | 2/2006 | Zhou et al. | |
| 2007/0015996 A1* | 1/2007 | Camus et al. | 600/407 |
| 2007/0038061 A1 | 2/2007 | Huennekens et al. | |
| 2007/0225606 A1 | 9/2007 | Naghavi et al. | |
| 2010/0241404 A1 | 9/2010 | Taylor et al. | |
| 2012/0041739 A1* | 2/2012 | Taylor | 703/11 |
| 2013/0060133 A1* | 3/2013 | Kassab | A61B 6/504 |
| | | | 600/431 |
| 2013/0132054 A1* | 5/2013 | Sharma | G06F 19/12 |
| | | | 703/9 |
| 2014/0243663 A1† | 8/2014 | Taylor | |
| 2014/0378850 A1* | 12/2014 | Plakas | A61B 5/026 |
| | | | 600/504 |
| 2015/0282765 A1* | 10/2015 | Goshen | A61B 6/032 |
| | | | 600/408 |

OTHER PUBLICATIONS

Morris et al. "Virtual (Computed) Fractional Flow Reserve: Current Challenges and Limitations." JACC: Cardiovascular Interventions: 8(8): pp. 1009-1017. 2015.*
Morris et al. "Virtual Fractional Flow Reserve From Coronary Angiography: Modeling the Significance of Coronary Lesions : Results From the VIRTU-1 (VIRTUal Fractional Flow Reserve From Coronary Angiography) Study." JACC: Cardiovascular Interventions: 6(2): pp. 149-157. 2013.*
Taylor et al. "Computational Fluid Dynamics Applied to Cardiac Computed Tomography for Noninvasive Quantification of Fractional Flow Reserve : Scientific Basis." JACC: 61(22): pp. 2233-2241. 2013.*
Koo et al. "Diagnosis of Ischemia-Causing Coronary Stenoses by Noninvasive Fractional Flow Reserve Computed From Coronary Computed Tomographic Angiograms : Results From the Prospective Multicenter Discover-Flow (Diagnosis of Ischemia-Causing Stenoses Obtained via Noninvasive Fractional Flow Reserve) Study." JACC: 58(19): pp. 1989-1997. 2011.*
Min et al. "Rationale and design of the DeFACTO (Determination ofFractional Flow Reserve by Anatomic Computed Tomographic AngiOgraphy) study." JACC: 5(5): pp. 301-309. 2011.*
Martus et al. "Fractional Flow Reserve Estimation by Coronary Computed Tomography Angiography." JACC: 59(15): pp. 1410-1411. 2012.*
Search Report and Written Opinion from corresponding EP Application No. 13154938.8-1657 dated Jun. 13, 2013.
Koo et al., "Diagnosis of Ischemia-Causing Coronary Stenoses by Noninvasive Fractional Flow Reserve Computed From Coronary Computed Tomographic Angiograms", Journal of the American College of Cardiology, Elsevier, New York. NY, US, vol. 58, No. 19, pp. 1989-1997, Jun. 27, 2011.
Min et al., "Rationale and design of the DeFACTO (Determination of Fractional Flow Reserve by Anatomic Computed Tomographic AngiOgraphy) study", Journal of Cardiovascular Computed Tomography, Elsevier, Amsterdam, NL, vol. 5, No. 5, pp. 301-309, Aug. 3, 2011.
Pijls et al., "Experimental basis of determining maximum coronary, myocardial, and collateral blood flow by pressure measurements for assessing functional stenosis severity before and after percutaneous transluminal coronary angioplasty", Circulation, vol. No. 87, pp. 1354-1367, 1993.

* cited by examiner
† cited by third party

FRACTIONAL FLOW RESERVE ESTIMATION

CROSS-REFERENCE TO RELATED APPLICATIONS

This application is a continuation of U.S. patent application Ser. No. 13/408,886, entitled "Fractional Flow Reserve Estimation", filed Feb. 29, 2012, which is herein incorporated by reference in its entirety for all purposes.

BACKGROUND

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, Coronary Computed Tomography Angiography (CCTA) is an imaging application that has evolved with the introduction and improvement of computed tomography (CT), an imaging technology based on the observed transmission of X-rays through the patient for a range of angular positions that is sufficient for image reconstruction. With the introduction of multi-slice CT scanners (e.g., 4-slice, 16-slice, 64-slice and so forth) and faster rotation speeds (e.g., about 0.35 seconds to about 0.5 seconds for a full gantry rotation), it has become possible to generate useful images of the heart. With current high-resolution (both spatial and temporal), 64-slice scanners, image quality is sufficient for CCTA to provide clinicians an imaging technique that has high negative predictive value (ratio of true negative classifications to the total number of negative classifications). In other words, the technology, CCTA is very accurate in assessing patients that do not have disease. However, false positives may still occur at undesired frequency, reducing the positive predictive value of CCTA (ratio of true positive classifications to the total number of positive classifications). As such, advances are needed to improve the clinical utility of CCTA.

Further, CCTA typically provides only anatomical information of the heart and vascular structures. It may also be useful to provide various functional assessments, such as of territorial myocardial perfusion, which would be useful in determining if a narrowing in a coronary vessel (stenosis) due to atherosclerotic plaque is affecting cardiac function. There are various methods to assess cardiac function: treadmill stress test, stress echocardiogram, myocardial stress perfusion imaging (using Single Photon Emission Computed Tomography (SPECT), Positron Emission Tomography (PET), CT perfusion, or invasive assessment of cardiovascular hemodynamics (fractional flow reserve (FFR)).

Combining both anatomical information and a correlated per territory assessment of resulting cardiac function may be useful in the clinical evaluation of cardiac disease. One approach, percutaneous coronary intervention (PCI), may provide this capability using anatomical information via projection coronary angiography and functional information through coronary blood pressure measurements from a transducer in the coronary vasculature. However, these procedures are highly invasive and frequently turn out to be unnecessary (diagnostic) (e.g., in approximately ⅓ of the procedures in patients with multi-vessel disease).

BRIEF DESCRIPTION

In one embodiment, a method is provided for assessing hemodynamic information. The method includes the act of generating or acquiring anatomic information comprising at least a location and topology of a narrowing of a blood vessel. Blood flow information comprising at least flow information in one or more vessels proximal to the location of the narrowing is also generated or acquired. Hemodynamic information is estimated based at least on the anatomic information and the blood flow information.

In a further embodiment, one or more non-transitory computer-readable media are provided. The computer-readable media encode one or processor-executable routines. The one or more routines, when executed by a processor, cause acts to be performed comprising: accessing anatomic information comprising at least a location and topology of a narrowing of a blood vessel; accessing or acquiring blood flow information comprising at least flow information corresponding to one or more vessels proximal to the narrowing; and estimating hemodynamic information based at least on the anatomic information and the blood flow information.

In an additional embodiment, a processor-based system is provided. The processor-based system comprises a storage encoding one or more processor-executable routines. The routines, when executed cause acts to be performed comprising: generating or acquiring anatomic information comprising at least a location and topology of a narrowing of a blood vessel; generating or acquiring blood flow information comprising at least flow information corresponding to one or more vessels proximal to the narrowing; and estimating hemodynamic information based at least on the anatomic information and the blood flow information. The processor-based system also comprises a memory configured to encode the one or more processor-executable routines prior to execution and a processing component configured to access and execute the one or more routines when encoded by the memory.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
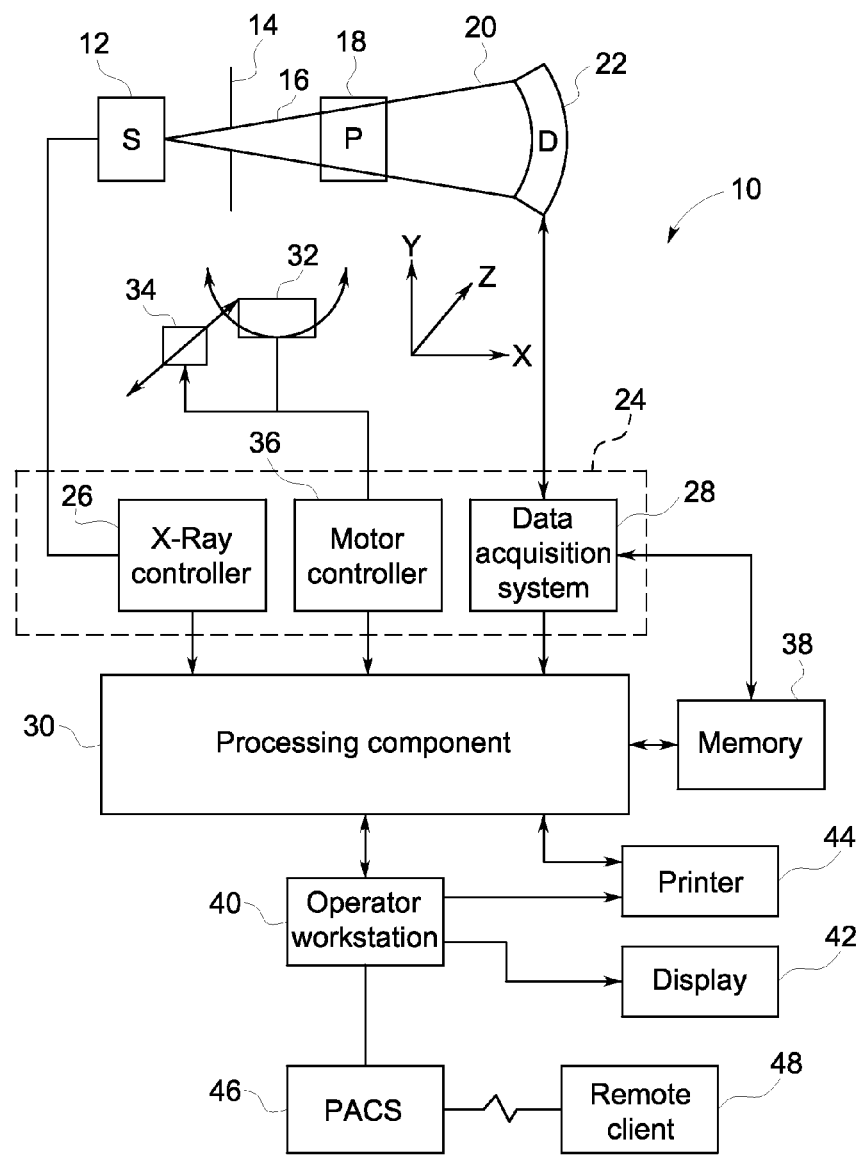
FIG. 1 is a block diagram depicting components of a computed tomography (CT) imaging system, in accordance with aspect of the present disclosure.

Development of a non-invasive method to assess coronary anatomy and associated per territory evaluation of myocardial tissue function may be a useful tool in providing cardiac healthcare. Such a non-invasive approach may provide reduced patient morbidity/mortality due to the elimination of unnecessary interventional procedures as well as a reducing healthcare costs for cardiac care. With this in mind the present approach provides a non-invasive methodology for both anatomical and functional assessment of cardiac hemodynamics. One embodiment of the present approach utilizes the anatomical information provided by Coronary Computed Tomography Angiography (CCTA) and estimation of coronary blood flow by ultrasound as input to a computational fluid dynamics (CFD) model. Though CT approaches are discussed herein, the present approaches may also be implemented using anatomical data measured and derived using other suitable imaging modalities, such as magnetic resonance imaging (MRI) or interventional X-ray imaging. Although not limiting cases for X-ray imaging, application of the techniques described herein using data acquired with a CT system are well-suited for assessment of chronic coronary artery disease (i.e.—non-emergency situations), whereas applications using data acquired with an interventional X-ray system are well-suited for the acute imaging environment (i.e. emergency situations). Explicit mention of CT imaging in the techniques described herein is merely intended to facilitate explanation by providing an example in a clinical context, and is not meant to be limiting with respect to the modalities that may be employed. For example, acquisition of anatomical information using an interventional X-ray system is also envisioned.

In one such implementation, the CFD model utilizes the (1) geometrical characterization of coronary vessel boundaries, tissue differentiation using multi-energy analysis, and regions of stenosis using CT data, and (2) coronary flow information derived from spectral Doppler ultrasound data as a boundary condition to compute the pressure differential across a stenotic lesion. In such an implementation, these data, and perhaps additional data such as peripheral blood pressure measurements, may be used to estimate the myocardial fractional flow reserve resulting from the diseased vessel. The anatomical data and functional data can be combined, such as using a Bayesian classification scheme, to facilitate a more sensitive and specific assessment of the disease. In addition to the estimated myocardial fractional flow reserve, CT perfusion assessment information, treadmill stress data, and SPECT/PET functional information are just a few of the metrics comprising the functional information that may be used with the Bayesian classification scheme.

With the foregoing in mind, it may be useful to provide a brief description of basic components of a CT system and of an ultrasound system that may be used in accordance with the present disclosure. For example, turning to FIG. 1, a CT imaging system 10 is depicted that may be used to acquire X-ray attenuation data at a variety of view angle positions as the gantry rotates around a patient; these data would be suitable for CCTA. In the embodiment illustrated in FIG. 1, imaging system 10 includes a source of X-ray radiation 12 positioned adjacent to a collimator 14. The X-ray source 12 may be an X-ray tube, a distributed X-ray source (such as a solid-state or thermionic X-ray source) or any other source of X-ray radiation suitable for the acquisition of medical or other images.

The collimator 14 permits X-rays 16 to pass into a region in which a patient 18, is positioned. In the depicted example, the X-rays 16 are collimated to a cone-shaped beam and/or a fan-shaped beam that passes through the imaged volume. A portion of the X-ray radiation 20 passes through or around the patient 18 (or other subject of interest) and impacts a detector array, represented generally at reference numeral 22. Detector elements of the array produce electrical signals that represent the intensity of the incident X-rays 20. These signals are acquired and processed to reconstruct images of the features within the patient 18. When considering interventional X-ray systems, the X-ray detector may comprise a flat-panel digital detector.

Source 12 is controlled by a system controller 24, which furnishes both power, and control signals for CCTA examination sequences. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In the embodiment illustrated in FIG. 1, system controller 24 is coupled to a rotational subsystem 32 and a linear positioning subsystem 34. The rotational subsystem 32 enables the X-ray source 12, collimator 14 and the detector 22 to be rotated one or multiple turns around the patient 18, such as rotated primarily in an x, y-plane about the patient. It should be noted that the rotational subsystem 32 might include a gantry upon which the respective X-ray emission and detection components are disposed. Thus, in such an embodiment, the system controller 24 may be utilized to operate the gantry.

The linear positioning subsystem 34 may enable the patient 18, or more specifically a table supporting the patient, to be displaced within the bore of the CT system 10, such as in the z-direction relative to rotation of the gantry. Thus, the table may be linearly moved (in a continuous or step-wise fashion) within the gantry to generate images of particular areas of the patient 18. In the depicted embodiment, the system controller 24 controls the movement of the rotational subsystem 32 and/or the linear positioning subsystem 34 via a motor controller 36.

In general, system controller 24 commands operation of the imaging system 10 (such as via the operation of the source 12, detector 22, and positioning systems described above) to execute examination protocols (such as CCTA protocols) and to process acquired data. For example, the system controller 24, via the systems and controllers noted above, may rotate a gantry supporting the source 12 and detector 22 about a subject of interest so that X-ray attenuation data may be obtained at a variety of view angle positions relative to the subject. In the present context, system controller 24 may also include signal processing circuitry, associated memory circuitry for storing programs and routines executed by the computer (such as routines for executing image processing techniques described herein), as well as configuration parameters, image data, and so forth.

In the depicted embodiment, the image signals acquired and processed by the system controller 24 are provided to a processing component 30 for measurement data processing and/or reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image reconstruction, as described below.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images and/or otherwise operate the system 10 using the operator workstation 40. For example, a display 42 coupled to the operator workstation 40 may be utilized to observe the reconstructed images and to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the CT imaging system 10 separately, these various components may be provided within a common platform or in interconnected platforms. For example, the processing component 30, memory 38, and operator workstation 40 may be provided collectively as a general or special purpose computer or workstation configured to operate in accordance with the aspects of the present disclosure. In such embodiments, the general- or special-purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition. In a present embodiment, the CT imaging system 10 may be a system suitable for coronary CT angiography (CCTA), a technique employed for imaging the coronary vasculature. An example of such a system is a Discovery CT750HD available from General Electric Company. Alternatively, an interventional X-ray system providing coronary X-ray angiography may provide the requisite information. An example of such a system is a Discovery IGS 730 available from General Electric Company.

Figure 2:
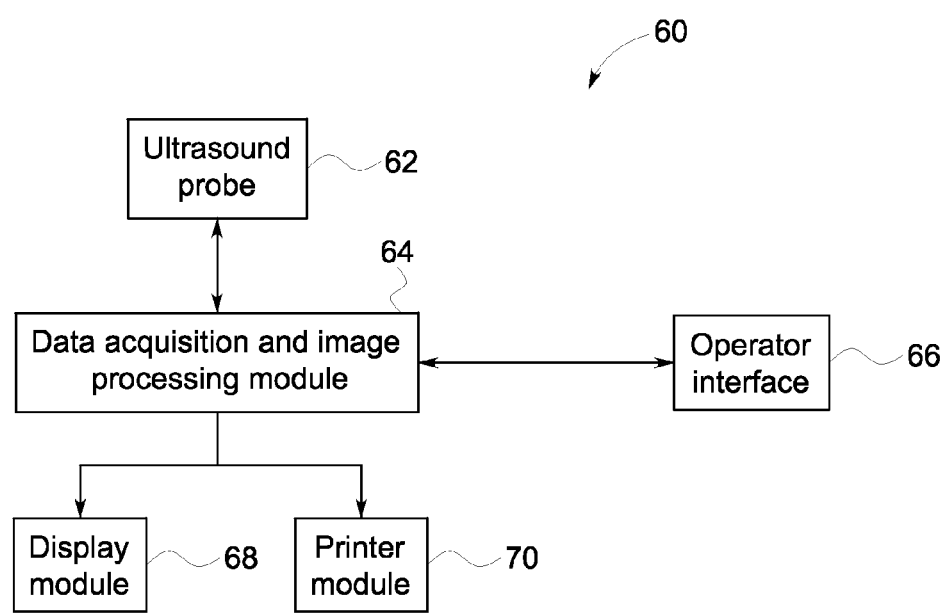
FIG. 2 is a block diagram depicting components of an ultrasound imaging system, in accordance with aspect of the present disclosure.

As noted above, in addition to anatomical image data derived using a CT system, MRI system, or interventional X-ray system (or other suitable anatomic imaging modality), functional data may also be acquired and utilized in the present approach. For example, turning to FIG. 2, an ultrasound system 60 suitable for use in accordance with the present disclosure is depicted.

As depicted, the ultrasound imaging system 60 includes an ultrasound probe 62, a data acquisition and image-processing module 64, an operator interface 66, a display module 68 and a printer module 70. The ultrasound imaging system 60 uses the ultrasound probe 62 for transmitting a plurality of ultrasound signals into an object, such as into the cardiac or thoracic region of a patient being imaged, and for receiving a plurality of reflected ultrasound signals therefrom. The ultrasound probe 62 may include an array of transducer elements for transducing mechanical or electrical energy to acoustic energy, and vice versa, to facilitate this process. In certain embodiments, the ultrasound probe 62 can be hand-held or mechanically positioned such as by using a robotic assembly, or otherwise placed in position. The ultrasound system 60 may employ 2D beam formation technology with mechanically swept beams or 2D phase-array technology to obtain the desired volumetric ultrasound data, as discussed herein.

The data acquisition and image-processing module 64 sends signals to and receives information from the ultrasound probe 62. Thus, the data acquisition and image-processing module 64 controls strength, width, duration, and a frequency of the plurality of ultrasound signals transmitted by the ultrasound probe 62, and receives the information contained in the plurality of reflected ultrasound signals from the object to a plurality of discernible electrical and electronic signals. Once the information is obtained, an ultrasound image of the features or characteristics of interest within the imaged volume is reconstructed/presented in accordance with generally known reconstruction/presentation techniques. In addition, other forms of information, such as blood flow, can be derived from ultrasound data.

The operator interface 66 may include a keyboard, a mouse, and other user interaction devices. The operator interface 66 can be used to customize a plurality of settings for an ultrasound examination, and for effecting system level configuration changes. The operator interface 66 is connected to the data acquisition and image-processing module 64 and may be used to command the data acquisition and image-processing module 64 to display information on the display module 68 or to print information on the printer module 70. For example, the display module 68 may receive information from the data acquisition and image-processing module 64 and presents the image of the region of interest imaged by the ultrasound probe 62. The printer module 70 may be used to produce a hard copy of the ultrasound image in either gray-scale or color.

In a present embodiment, the ultrasound system 60 is capable of acquiring one or more types of volumetric flow information within a vessel. That is, the plurality of reflected ultrasound signals received by the ultrasound probe 62 are processed to derive a spatial representation that describes one or more flow characteristics of blood within the imaged vasculature. For example, in one embodiment, the ultrasound system 60 is suitable for deriving spectral or color-flow type Doppler information pertaining to one or more aspects of blood flow or velocity within the region undergoing imaging (e.g., spectral or color flow Doppler velocity information for planar or volume flow estimation). Similarly, various volumetric flow algorithms may be used to process or integrate acquired ultrasound data to generate volumetric flow information corresponding to the sample space inside a blood vessel.

With the foregoing systems in mind both CCTA and ultrasound data may be acquired in accordance with an implementation of a present embodiment. For example, with respect to the acquisition of CCTA data, customary CCTA protocols may be employed in some implementations, including administration of a vasodilator (such as adenosine). A preliminary contrast bolus injection may be made to determine the transit time from the peripheral venous injection site to contrast enhancement in the aorta. Once this delay is determined, and the patient's heart rate is estimated, the scanning parameters of the data acquisition are appropriately selected: gantry rotation speed, number of sectors required if performing a multi-sector acquisition, cardiac phase-percentage of the R-R interval of the cardiac cycle, helical protocol, axial step-and-shoot protocol, projection data padding, half-scan X-ray tube current modulation, and so forth. Based on the angular range over which projection data are acquired, multi-phasic reconstructions can be computed. For the collection of multi-phasic reconstructions, the volumetric reconstruction with the best image quality may be used for diagnosis. The coronary vessels are then segmented. Data may be presented to the clinician in a variety of formats: axial images, volume renderings, multi-planar reformats along the coronary vessels, display of vessel cross section, etc. From these data, the location and severity of the stenosis can be assessed.

Figure 3:
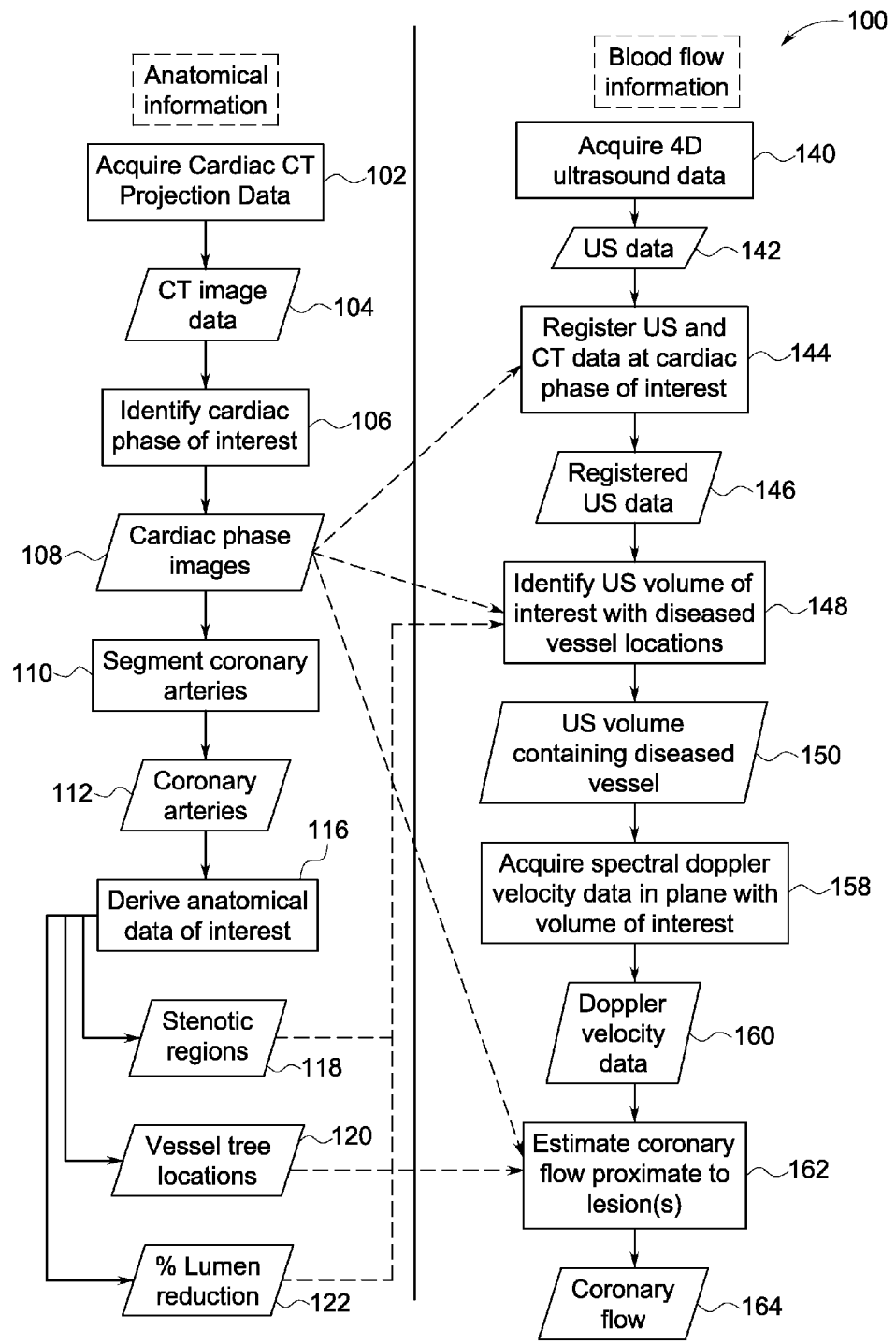
FIG. 3 depicts a process flow diagram of steps corresponding to one implementation of data acquisition and analysis in accordance with aspect of the present disclosure.

This process is summarized in FIG. 3, which depicts a process flow overview 100 for acquisition of both CCTA and ultrasound data. Turning to FIG. 3, with respect to the CCTA acquisition and processing, high-resolution CT image data 104 are reconstructed from projection data acquired (block 102) using a cardiac CT imaging protocol suitable for the CT imaging system 10. Phasic reconstructions are generated and used to discern (block 106) the cardiac phase (denoted by cardiac phase images 108) with the best image quality. If using an interventional X-ray system, full-rotation or partial-rotation spin acquisitions are used to collect the requisite data for image reconstruction, using standard CT, tomosynthesis, or compressed-sensing reconstruction techniques. The coronary arteries 112 are segmented (block 110) with respect to the remainder of the image data. The image data corresponding to the segmented coronary arteries 112 is used to derive (block 116) anatomical data of interest, such as to identify stenotic regions using multi-planar reformats, and so forth, including the locations 118 of the lesions, vessel tree locations 120, and the percentage of narrowing 122 within the respective lumens.

Once the CT data are evaluated and atherosclerotic lesions are identified, ultrasound data is used to compute coronary flow information in the diseased vessels, and, if needed, main branch vessels leading to the aortic root. In particular, in one implementation, the volumetric CT, including the identification of the location(s) of the stenotic lesion, is used to guide the ultrasound acquisitions. In such an implementation, an ultrasound transducer in an appropriate transthoracic or transesophogeal orientation allowing "access" to the identified coronary artery segments measures volumetric time-varying 2D or 3D ultrasound information. By selecting the appropriate cardiac phase based on the CT data—such as during the quiescent phase of the cardiac cycle (diastole), the selected 2D or 3D ultrasound data is registered to the CT data. This multi-modality registration allows identification of the volume(s) of interest where spectral or color-flow Doppler ultrasound information (or other suitable ultrasound information), as discussed below, is used for blood flow estimation.

In one embodiment, spectral Doppler ultrasound data is collected on a plane within a volume of interest comprising the coronary vessel and neighboring tissue. Using the mean velocity estimate within the plane of the volume of interest, the registered CT and spectral Doppler information will allow estimation of the vessel cross section, correction for the partial volume effect, and orientation of the ultrasound beam to the vessel, thereby enabling estimation of the flow within the coronary vessel. Furthermore, estimation of the precursor velocity data (and subsequent flow information) requires normalization to spectral Doppler signals completely embedded within a larger vessel; the aorta which is spatially proximal to the coronary vessels may be used for this purpose. Alternatively, techniques for estimating flow from spectral Doppler information collected from a volume within the imaging field of view may be employed. Additionally, although use of ultrasound to estimate velocity/flow information is specifically mentioned herein, other suitable imaging techniques may be utilized to estimate flow information. For example, phase-contrast MRI may be utilized to generate the requisite velocity/flow information. Similarly, ultrasound techniques other than those mentioned that are suitable for acquiring the intra-vessel blood flow information (e.g., velocity) may also be employed.

This process is also summarized in FIG. 3. Turning to FIG. 3, transthoracic or transesophogeal 3D or 4D (i.e., temporally-varying 2D or 3D data) ultrasound data 142 is initially acquired (block 140). Utilizing the reconstructed CT data at a phase of interest, the 2D or 3D ultrasound data is registered (block 144) with the CT data at the identified cardiac phase to generate a set of registered ultrasound data 146. Utilization of the CT data for registration purposes with the ultrasound data is denoted by the dotted line in FIG. 3. In the depicted example, a volume of interest 150 for spectral Doppler ultrasound interrogation is identified (block 148) using the registration 146 with the CT image data and identified locations of atherosclerotic lesions. Velocity information 160 is acquired from a plane or volume within the volume of interest 150 using a spectral Doppler acquisition (block 158). Alternatively, Doppler information for volume flow estimation may be acquired. Transthoracic or transesophageal acquisition protocols, or other acquisition protocols that provide the requisite Doppler information, may be utilized. Flow information 164 in the coronary vessel may be estimated (block 162) using geometric information provided by the CT images and identified locations of atherosclerotic lesions. Again, the utilization of CT data for facilitating the ultrasound acquisition/data processing is identified by the dotted lines in FIG. 3.

Figure 4:
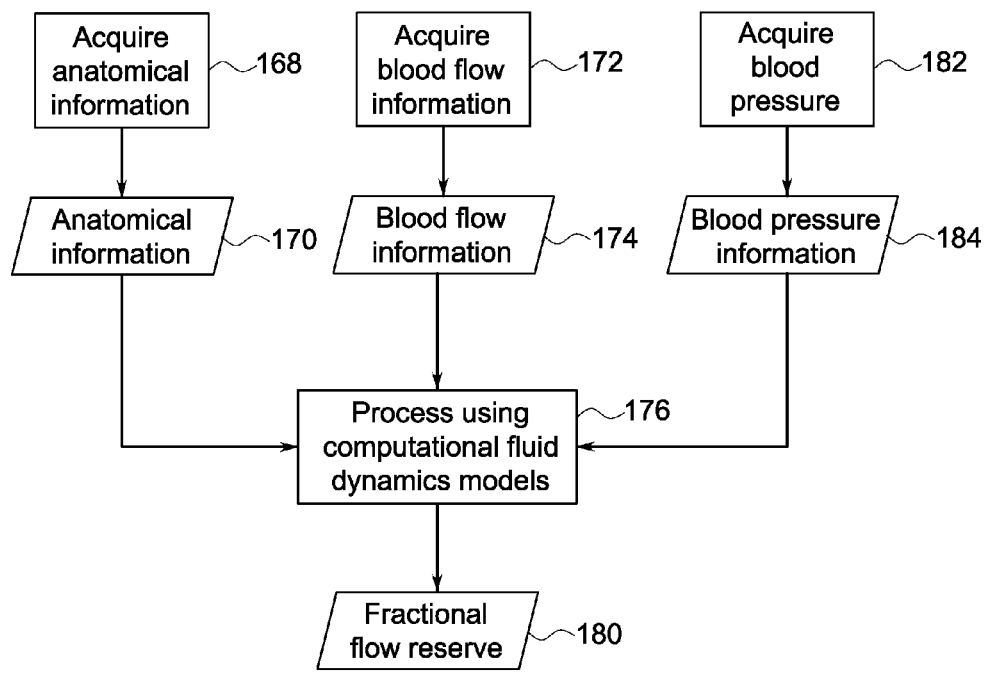
FIG. 4 depicts a flow diagram of the estimation of a fractional flow reserve in accordance with aspect of the present disclosure.

Once the CCTA and ultrasound acquisitions have been executed, the data are used as inputs to computational fluid dynamics models to compute additional hemodynamic information. For example, turning to FIG. 4, the anatomical information 170 acquired (block 168) by CCTA (or other suitable anatomical imaging modalities, such as MRI or interventional X-ray) and the blood flow information 174 acquired (block 172) by spectral Doppler ultrasound are processed (block 176) using computational fluid dynamics models to generate an estimate of a fractional flow reserve 180. In certain implementations, an acquired (block 182) blood pressure 184 may also be used as an input to the models to allow estimation of the upstream and downstream pressure with respect to the stenosis. In such implementations, the CCTA information (e.g., anatomical information 170) may be used to generate the geometry of the coronary vasculature proximal to the stenotic lesion(s). The ultrasound flow information (e.g., blood flow information 174) may be used to provide flow boundary conditions for the computational fluid dynamics model and the computational fluid dynamics model computes the transstenotic pressure across the atherosclerotic lesion (allowing computation of the pressure drop or the percentage pressure drop across one or more lesions of interest), as discussed below. In certain implementations, the additional information derived by the various imaging modalities may also be employed, such as CT perfusion data, stress echocardiography, tissue strain measurements, treadmill stress information, and/or functional SPECT/PET information—to name a few.

The fractional flow reserve 180 is defined as the ratio of the myocardial blood flow resulting from the stenosis to normal myocardial blood flow assuming a normal vasculature. Measurements are typically obtained when the myocardial vascular bed resistance is at its minimum and assumed constant. This situation occurs during hyperemia, which may be induced by administration of a vasodilator such as adenosine. The total resistance to blood flow can be conceptualized as the resistance due to the stenotic lesion and the remaining vascular bed resistance. The derivation of myocardial fractional flow reserve may be represented as:

$$FFR_{myocardium} = \frac{P_{distal} - P_{venous}}{P_{aorta} - P_{venous}} \quad (1)$$

where: $P_{distal}$ the mean arterial pressure distal to the stenotic lesion, $P_{aorta}$ is the mean aortic pressure (measured at aortic root), and $P_{venous}$ is the mean venous pressure (measured at right atrium). In clinical practice, the pressure measurements distal to and proximal to the stenotic lesion are typically measured to predict myocardial fractional flow reserve and the venous pressure (~3-8 mmHg) is often ignored such that:

$$FFR_{myocardium} \approx \frac{P_{distal}}{P_{aorta}} \quad (2)$$

In conventional interventional approaches a single catheter may be inserted in the femoral artery, threaded to the aortic ostium, positioned within a coronary vessel, and located proximate to the stenotic lesion for the purpose of either diagnosis of disease and/or a therapeutic intervention. However, as noted above, embodiments of the present approach use acquired coronary CT angiography data 170 and an estimation of the blood flow 174 in the coronary segment in conjunction with computational fluid dynamics to compute the transstenotic pressure. In particular, the CT data provides the anatomical information of the vasculature (vessel length, diameter, extent of stenosis, stenosis composition, vessel characteristics such as elasticity, and so forth). The ultrasound data provides the boundary condition: flow through the vessel. Given these data, anatomical structures are segmented into small structures (fine mesh elements with dimensions that depend on the gradient of the quantity to be computed). The governing differential equations—appropriately discretized, with the boundary conditions—are used to find the solution to the pressure throughout the defined domain. As mentioned previously, the anatomical information 170 may be generated from CT data, MRI data, interventional X-ray data, and so forth.

Figure 5:
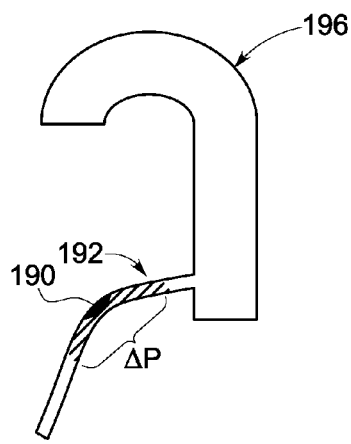
FIG. 5 graphically depicts a stenosis located within a primary coronary branch in accordance with aspect of the present disclosure.
Figure 6:
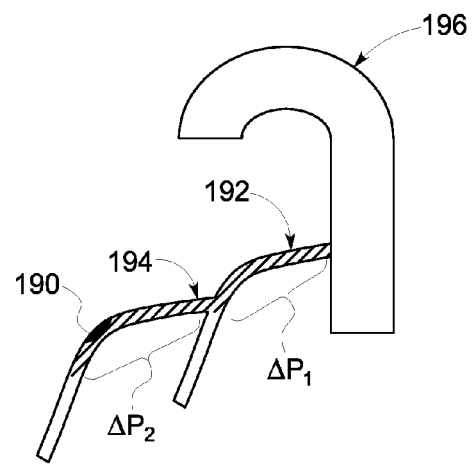
FIG. 6 graphically depicts a stenosis located within a secondary coronary branch in accordance with aspect of the present disclosure.

In one implementation, a local segment of the coronary vasculature is used for estimating fractional flow reserve. Turning to FIGS. 5 and 6, two scenarios for possible stenosis location are depicted: FIG. 5 depicts a stenosis 190 located on a primary coronary branch 192 relative to the aortic arch 196 and (2) FIG. 6 depicts a stenosis 190 located on a secondary coronary branch 194 relative to the aortic arch 196. Obviously, the identified stenosis 190 can be on any branch of the coronary vasculature, but the depicted representative examples are useful in elucidating aspects of the present approach.

For the primary branch stenosis of FIG. 5, the CFD models compute the transstenotic pressure difference:

$$\Delta P = P_{aorta} - P_{distal} \quad (3)$$

The quantity that may be desired is the ratio of the two pressures. If the pressure in the aorta can be non-invasively estimated, the transstenotic pressure difference can be subtracted from the aortic pressure to estimate the distal coronary pressure. With these two quantities, the myocardial fractional flow reserve can then be computed. In one implementation, the mean arterial blood pressure in the brachial artery, estimated with a standard blood pressure cuff, may be used to approximate the mean aortic pressure, either as is or modified with a population-relevant, demographic-relevant scaling factor.

For the second scenario represented in FIG. 6, the identified stenosis is on a secondary coronary branch 194. Using the CFD model of the diseased segment up to the bifurcation allows estimation of the transstenotic pressure differential ($\Delta P_2$). As in the previous example, it may be desired to use the estimate of the aortic pressure to compute the distal coronary pressure ($P_{distal}$); however, there is an additional branch of coronary vasculature (primary branch) that connects the aortic root to the bifurcation. Therefore, the pressure differential ($\Delta P_1$) will need to be estimated across the primary branch as well. For this case—or any other case where the diseased vessel is not the primary branch—coronary blood flow is estimated in the branches leading to the diseased vessel to be able to compute the distal coronary pressure.

$$P_{distal} = P_{aorta} - \Delta P_1 - \Delta P_2 \quad (4)$$

where $\Delta P_1$ is the pressure drop across the primary branch leading to the bifurcation and $\Delta P_2$ is the pressure drop across the lesion.

For each sequential branch, CFD models can be used to estimate the differential pressure at the extents of each segment. Although more complex than the case where the stenotic lesion is in the primary coronary branch 192, this method is more computationally tractable than modeling the entire coronary vasculature, chambers of the heart, major vessels connecting to the heart, and vascular bed resistances, as is conventionally done.

While the preceding describes one possible implementation, it is to be understood that other implementations and uses are also contemplated. For example, in a further implementation taking into account Doppler angle correction (as may be determined from a CT reconstruction of the coronary artery in question), a modified form of the Bernoulli equation may be employed to estimate the pressure drop across an obstruction. For example, flow velocity may be determined at the obstruction and before the obstruction. The flow velocity data at the obstruction and before the obstruction may be used in solving a modified Bernoulli equation (such as those modifications of the Bernoulli equation used in assessing pressure drop across regurgitant cardiac valves) to derive an estimate of the pressure drop across the obstruction.

Though coronary applications are discussed herein so as to provide examples and to facilitate explanation, it should be appreciated that the present approaches may also be employed in other contexts where blood flow about an organ is of interest. In an approach that is similar to the processes disclosed herein (FIG. 3 & FIG. 4), the anatomical information ascertained from acquiring (using general-purpose or specialized acquisition schemes) and processing (segmentation, enhancement, visualization, etc.) CT data, interventional X-ray data, MRI data, and/or data from other imaging modalities, may be registered to ultrasound data and used to identify vascular segments in a volume of interest within the patient. Further, Doppler ultrasound data may be acquired within the volume of interest for determination of vascular velocity/flow information. Collectively, the imaging data (anatomical information) and the ultrasound data (defining boundary conditions such as flow) may be provided as input to a computational fluid dynamics framework to generate additional hemodynamic information, such as differential pressures within the vasculature, tortuosity of flow, etc. As mentioned previously, imaging modalities other than ultrasound, such as phase-contrast MRI, may be utilized for generating the velocity/flow information. In some situations, auxiliary information, such as peripheral blood pressure measurement, may be used to facilitate hemodynamic assessment. As with cardiac imaging, the generalized goals of performing these processes are to better understand the disease state of the targeted anatomy and to facilitate subsequent therapeutic procedures (for example, stratify patients that will benefit from drug therapy versus interventional procedures, facilitate interventional procedures themselves, etc.). As discussed previously, these and other confirmatory and/or complementary data may be used within a Bayesian decision-making framework to improve the positive predictive value and/or negative predictive value of the specific evaluation/procedure. Although not meant to be limiting, some examples of clinical evaluations utilizing the present approaches in organs other than the heart are hemodynamic assessment of peripheral artery disease (stenosis in the iliac arteries, common femoral arteries, popliteal arteries, brachial arteries, etc.), disease of the liver (stenosis in the hepatic artery, etc.), disease of the kidneys (stenosis in the renal artery, etc.), or disease in the neuro-vasculature (stenosis in the carotid artery, reduction in tissue perfusion pressure, etc.).

Figure 7:
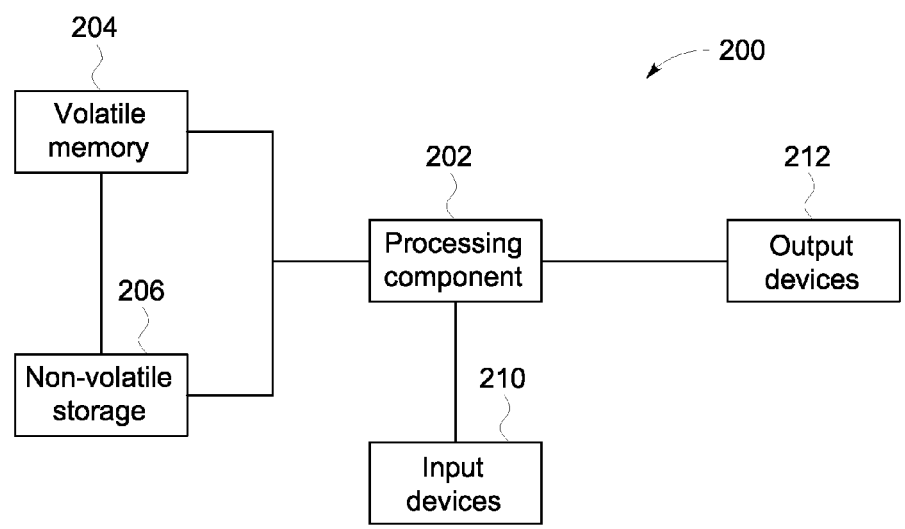
FIG. 7 is a block diagram depicting components of a processor-based system suitable for implementing certain of the present embodiments, in accordance with aspect of the present disclosure.

While some or all of the preceding steps and calculations may be performed on one or both of the ultrasound system 60 and/or the CT imaging system 10, in other embodiments, some or all of the steps and calculations may be performed by a processing system 200 (FIG. 7) capable of receiving data generated by the ultrasound system 60 and/or the CT imaging system 10. For example, turning to FIG. 7, an example of one such system is depicted.

In the depicted system, the processing component 202 may be one or more conventional microprocessors. The data collected by the ultrasound system 60 and/or the CT imaging system 10 may be communicated to the processing component 202 directly (such as via a network connection) or via intermediary steps (such as storage in an accessible database or on a storage medium). Any type of computer- or processor-readable media (e.g., a memory 204 or a storage device 206) suitable for storing data and/or processor-executable code might be utilized or accessed by such an exemplary system 200. For example, the volatile memory 204 may include one or more optical, magnetic, and/or solid state memory storage structures. Similarly, the non-volatile storage 206 may include one or more of a solid state or magnetic hard drive, optical disks, and so forth. Moreover, the memory 204 and/or storage 206 may be located at the processing system 200 and/or may include remote storage or memory for storing data, processing parameters, and/or routines for data analysis, as described above. In one embodiment, one or both of the non-volatile storage 206 or volatile memory 204 may store routines or other processor-executable code implementing the approach discussed herein, such as for accessing and processing the relevant CT and ultrasound data to generate measures including, but not limited to, fractional flow reserve.

The processing component 202 may be configured to receive commands and processing parameters from an operator via input devices 210, such as a keyboard and/or mouse. An operator may control the system 200 via the input devices 210. Thus, the operator may cause the processing of CT and/or ultrasound data and the calculation of a fractional flow reserve using the input devices 210. Likewise, the input devices 210 may include one or more network connections (wired or wireless) or other data connections by which commands and/or data may be provided to the processing component 202.

The processing system 200 may output calculated results or measurements via one or more output devices 212. For example, the output devices 212 may include a display or printer suitable for displaying or printing a calculated measure (such as a fractional flow reserve) or a report that includes one or more such measures.

Technical effects include calculation of a fractional flow reserve based on inputs provided to a computational fluid dynamics model. In one implementation, the inputs to the computational fluid dynamics model are derived from anatomical imaging data (such as may be derived from CT or interventional X-ray systems) and from ultrasound imaging data that may provide flow boundary conditions for the computational fluid dynamics model. Technical effects also include the non-invasive assessment of blood flow dynamics in and around a vascular obstruction, such as a stenotic lesion.

This written description uses examples to disclose the subject matter of interest, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A microprocessor-implemented method for assessing hemodynamic information, consisting essentially of:
acquiring vasculature images depicting at least a location and topology of a narrowing of a blood vessel;
segmenting the blood vessel from a remainder of the vasculature images to extract anatomical information representing the geometry of the blood vessel, wherein the anatomical information includes a location of a narrowing of the blood vessel, branch locations of the blood vessel, and a percentage of lumen reduction at the location of the narrowing, such that a localized region based on the location of the narrowing and the branch locations is determined;
non-invasively acquiring local blood flow information in at least one or more vessels proximal to the location of the narrowing;
quantifying a pressure drop across the narrowing based on the reduced section of the blood vessel and the acquired blood flow using a computational fluid dynamics model configured to receive the geometry of the blood vessel and the blood flow information;
calculating one or more numeric values quantifying hemodynamic characteristics based on the pressure drop; and
generating and outputting for review at least the one or more calculated numeric values quantifying the hemodynamic characteristics.

2. The method of claim 1, wherein the anatomical information further comprises one or more of a location of a vessel tree, a percentage of lumen reduction, or stenosis composition.

3. The method of claim 1, wherein the location of the narrowing of the blood vessel comprises a stenotic lesion.

4. The method of claim 1, wherein the local blood flow information comprises a flow boundary condition used in the computational fluid dynamics model.

5. The method of claim 1, comprising:
employing a computed tomography (CT) system to generate a set of CT image data;
segmenting arteries from one or more CT images; and
deriving the anatomical information based at least on the segmented arteries.

6. The method of claim 5, comprising:
employing an ultrasound system to generate a set of ultrasound data;
registering the ultrasound data to the CT image data;
identifying an ultrasound volume of interest based on the vascular images;
generating a set of velocity data for the ultrasound volume of interest; and
estimating at least the local blood flow information using the set of velocity data.

7. The method of claim 1, comprising:
employing an interventional X-ray system to generate a set of image data;
segmenting arteries from one or more reconstructed images; and
deriving the anatomical information based at least on the segmented arteries.

8. The method of claim 7, comprising:
employing an ultrasound system to generate a set of ultrasound data;
registering the ultrasound data to the set of image data;
identifying an ultrasound volume of interest based on the vasculature images;
generating a set of velocity data for the ultrasound volume of interest; and
estimating at least the local blood flow information using the set of velocity data.

9. One or more non-transitory computer-readable media encoding one or more processor-executable routines, wherein the one or more routines, when executed by a microprocessor, cause acts to be performed consisting essentially of:
accessing or acquiring vasculature images depicting at least a location and topology of a narrowing of a blood vessel;
segmenting the blood vessel from a remainder of the vasculature images to extract anatomical information representing the geometry of the blood vessel, wherein the anatomical information includes a location of a narrowing of the blood vessel, branch locations of the blood vessel, and a percentage of lumen reduction at the location of the narrowing, such that a localized region based on the location of the narrowing and the branch locations is determined;
accessing or acquiring non-invasively acquired local blood flow information for at least one or more vessels proximal to the narrowing;
quantifying a pressure drop across the narrowing based on the reduced section of the blood vessel and the acquired blood flow using a computational fluid dynamics model configured to receive the geometry of the blood vessel and the blood flow information;
calculating one or more numeric values quantifying hemodynamic characteristics based on the pressure drop; and
generating and outputting for review at least the one or more calculated numeric values quantifying the hemodynamic characteristics.

10. The one or more non-transitory computer-readable media of claim 9, wherein the anatomical information further comprises one or more of a location of a vessel tree, a percentage of lumen reduction, or stenosis composition.

11. The one or more non-transitory computer-readable media of claim 9, wherein the local blood flow information comprises a flow boundary condition used in the computational fluid dynamics model.

12. The one or more non-transitory computer-readable media of claim 9, wherein the one or more routines, when executed by the microprocessor, cause further acts to be performed comprising:
accessing a set of computed tomography (CT) image data;
segmenting arteries from one or more CT images; and
deriving the anatomical information based at least on the segmented arteries.

13. The one or more non-transitory computer-readable media of claim 12, wherein the one or more routines, when executed by the microprocessor, cause further acts to be performed comprising:
accessing a set of ultrasound data;
registering the ultrasound data to the one or more CT images;
identifying an ultrasound volume of interest based on the vasculature images;
generating a set of velocity data for the ultrasound volume of interest; and
estimating at least the local blood flow information using the set of velocity data.

14. The one or more non-transitory computer-readable media of claim 9, wherein the one or more routines, when executed by the microprocessor, cause further acts to be performed comprising:
accessing a set of interventional X-ray image data;
segmenting arteries from one or more images; and
deriving the anatomical information based at least on the segmented arteries.

15. The one or more non-transitory computer-readable media of claim 14, wherein the one or more routines, when executed by the microprocessor, cause further acts to be performed comprising:
accessing a set of ultrasound data;
registering the ultrasound data to the one or more images;
identifying an ultrasound volume of interest based on the vasculature images;
generating a set of velocity data for the ultrasound volume of interest; and
estimating at least the local blood flow information using the set of velocity data.

16. A microprocessor-based system, comprising:
a storage encoding one or more processor-executable routines, wherein the routines, when executed cause acts to be performed consisting essentially of:
acquiring vasculature images depicting at least a location and topology of a narrowing of a blood vessel;
segmenting the blood vessel from a remainder of the vasculature images to extract anatomical information representing the geometry of the blood vessel, wherein the anatomical information includes a location of a narrowing of the blood vessel, branch locations of the blood vessel, and a percentage of lumen reduction at the location of the narrowing, such that a localized region based on the location of the narrowing and the branch locations is represented;
acquiring non-invasively acquired local blood flow information comprising at least flow information corresponding to one or more vessels proximal to the narrowing;
quantifying a pressure drop across the narrowing based on the reduced section of the blood vessel and the acquired blood flow using a computational fluid dynamics model configured to receive the geometry of the blood vessel and the blood flow information;
calculating one or more numeric values quantifying hemodynamic characteristics based on the pressure drop; and
generating and outputting for review at least on the one or more calculated numeric values quantifying the hemodynamic characteristics;
a memory configured to encode the one or more processor-executable routines prior to execution; and
one or more microprocessors configured to access and execute the one or more routines when encoded by the memory.

17. The microprocessor-based system of claim 16, wherein the anatomical information further comprises one or more of a location of a vessel tree, a percentage of lumen reduction, or stenosis composition.

18. The microprocessor-based system of claim 16, wherein the blood flow information comprises a flow boundary condition used in the computational fluid dynamics model.

19. The microprocessor-based system of claim 16, wherein the location of the narrowing of the blood vessel comprises a stenotic lesion.

20. The microprocessor-based system of claim 16, wherein the routines, when executed by the one or more microprocessors, cause further acts to be performed comprising:
accessing a set of computed tomography (CT) image data;
segmenting arteries from one or more CT images; and
deriving the anatomical information based at least on the segmented arteries.

21. The microprocessor-based system of claim 20, wherein the routines, when executed by the one or more microprocessors, cause further acts to be performed comprising:
accessing a set of ultrasound data;
registering the ultrasound data to the one or more CT images;
identifying an ultrasound volume of interest based on the vasculature images;
generating a set of velocity data for the ultrasound volume of interest; and
estimating at least the local blood flow information using the set of velocity data.

22. The microprocessor-based system of claim 16, wherein the routines, when executed by the one or more microprocessors, cause further acts to be performed comprising:
accessing a set of interventional X-ray image data;
segmenting the arteries from one or more images; and
deriving the anatomical information based at least on the segmented arteries.

23. The microprocessor-based system of claim 22, wherein the routines, when executed by the one or more microprocessors, cause further acts to be performed comprising:
accessing a set of ultrasound data;
registering the ultrasound data to the one or more images;
identifying an ultrasound volume of interest based on the vasculature images;
generating a set of velocity data for the ultrasound volume of interest; and
estimating at least the local blood flow information using the set of velocity data.

* * * * *